US007008933B2

(12) United States Patent
Welzel (10) Patent No.: US 7,008,933 B2
(45) Date of Patent: Mar. 7, 2006

(54) PROCESS FOR PROPHYLAXIS AND THERAPY OF THROMBOTIC PROCESSES EMPLOYING HEPARIN HAVING PARTICULAR AVERAGE MOLECULAR WEIGHTS (76) Inventor: Dieter Welzel, Friedrich-Löffler-Strasse 24, D-90419, Nürnberg (DE)

(*) Notice: Subject to any disclaimer, the term of this patent is extended or adjusted under 35 U.S.C. 154(b) by 0 days.

(21) Appl. No.: 10/169,834

(22) PCT Filed: Dec. 22, 2000

(86) PCT No.: PCT/DE00/04674

§ 371 (c)(1),
(2), (4) Date: Oct. 25, 2002

(87) PCT Pub. No.: WO01/51525

PCT Pub. Date: Jul. 19, 2001

(65) Prior Publication Data
US 2003/0134823 A1  Jul. 17, 2003

(30) Foreign Application Priority Data
Jan. 10, 2000 (DE) ................. 100 00 602

(51) Int. Cl.
A61K 31/727 (2006.01)
C08B 37/10 (2006.01)
(52) U.S. Cl. .................. 514/56; 536/1.11; 536/21; 536/123.1; 536/124
(58) Field of Classification Search .............. 514/54, 514/56; 536/1.11, 123.1, 124, 21
See application file for complete search history.

(56) References Cited
PUBLICATIONS

Ekre, Hans-Peter T. "Inhibition Of Human And Guinea Pig Complement By Heparin Fractions Differing In Affinity For Antithrombin III Or In Average Molecular Weight", International Journal of Immunopharmacology, 1985, 7(2), 271-280.*
Alban et al., "The Anticoagulatory Impact of Low-Molecular-Weight Heparins is Subject to Product-specific Endogenous Modulation. The Significance of TFPI Release and Profibrinalytic Effect", American Congress of Cardiology, Orlando, Florida 1997.
Fareed et al., "Low molecular weight heparins: a development perspective", Abstract, Ashley Publications Ltd., ISSN 1354-3783—1997.
Fareed et al., "Biochemical and Pharmacologic Inequivalence of Low Molecular Weight Heparins", Annuals New York Academy of Science (1989) 556, pp. 333-353.
Nader et al., "Preclinical Differentiation of Low Molecular Weight Heparins", Seminars in Thrombosis and Hemostasis—vol. 25, Suppl. 3, 1999, pp. 63-72.
Fareed, "Antithrombotic Drugs in Traumatic Disorders Newer Developments and Future Perspectives", International Symposium 1992.
Boneu, "Low Molecular Weight Heparins: Are They Superior to Unfractionated Heparins to Prevent and to Treat Deep Vein Thrombosis", Trombosis Research, 100 (2000), V113-V120.
Sandset, "The Role of Tissue Factor Pathway Inhibitor as a Physiological Anticoagulant", 15th Intnl. Congress on Trhombosis (1998), pp. 183-189.
Wessler, M.D., "Thrombosis in the Presence of Vascular Statis", American Journal of Medicine, 1962, vol. 33, pp. 648-666.
Hirsh et al., "Low Molecular Weight Heparins", The Journal of The American Society of Hematology, vol. 79, No. 1, Jan. 1, 1992, pp. 1-17.
Kandrotas, "Heparin Pharmacokinetics and Pharmacodynamics", Clin. Pharmacokinet, 22(5); pp. 359-374, 1992.
Fareed et al., "Studies on the Antithrombotic Effects and Pharmacokinetics of Heparin Fractions and Fragments", Seminars in Thrombosis and Hemostasis, vol. 11, No. 1, (1985).
WO 01 02443—"Heparin Compositions That Inhibit Clot Associated Coagulation Factors", Jack Hirsh, Publication date: Jan. 11, 2001.
"Inhibition of Human and Guinea Pig Complement by Heparin Fractions Differing in Affinity for Antithrombin III Or In Average Molecular Weight", Hans-Peter T. Ekre, Researach and Development, Stockholm Sweden, pp. 271-277.
Kaiser et al., "Preclinical Biochemistry and Pharmacology of Low Molecular Weight Heparins in Vivo-Studies of Venous and Arterial Thrombosis", Seminars in Thrombosis and Hemostasis, vol. 25, Suppl 3, (1999), pp. 35-42.
Alban et al., "Plasma Levels of total and Free Tissue Factor Pathway Inhibitor (TFPI) as Individual Pharmacological Parameters of Various Heparins", Thromb Haemost 2001; 85; pp. 824-829.
GLYCODesign, Inc., Pharmaceutical and Biotechnology Companies, NetSci: The Biotech Yellow Pages, Seite 1, von 2, glycodesign.html.

* cited by examiner

Primary Examiner—James O. Wilson
Assistant Examiner—Ganapathy Krishnan
(74) Attorney, Agent, or Firm—Venable LLP; Thomas G. Wiseman (57) ABSTRACT A process for prophylaxis and therapy of thrombotic processes includes preparing heparin having an average molecular weight ranging from 10 to 11.5 kd; formulating a pharmaceutical preparation which includes the heparin; and employing the pharmaceutical preparation for prophylaxis and therapy of thrombotic processes. Preferably the heparin has an average molecular weight of 10.5 kd.

4 Claims, 8 Drawing Sheets

PROCESS FOR PROPHYLAXIS AND THERAPY OF THROMBOTIC PROCESSES EMPLOYING HEPARIN HAVING PARTICULAR AVERAGE MOLECULAR WEIGHTS

BACKGROUND OF THE INVENTION

1. Field of the Invention

The present invention generally relates to a novel medium molecular weight heparin, its preparation and use.

2. Description of the Related Art

Heparin was discovered by MacLean in 1916 and has been employed in medicine for more than 60 years. Its main field of application is antithrombotic prophylaxis and therapy. Meanwhile, heparin is used in medicine in two different forms. The first form is unfractionated heparin (UFH) which is recovered on an industrial scale from the lungs, livers or intestinal mucosae of cattle and pigs, and is obtained after proteolysis, separation of undesirable accompanying materials, such as fat and proteins, and bleaching. The second form is low molecular weight heparins (LMWH) which are obtained by the depolymerization of UFH.

The essential difference in the application of these two heparins resides in their different bioavailabilities. After subcutaneous injection of UFH, this is about 10–20% of the administered dose, while the bioavailability of LMWH is around 90% (R. J. Kandotas, Heparin Pharmacokinetics and Pharmacodynamics, Clinical Pharmacokinetics, 22(5): 359–374, 1992).

In the following Table 1, the essential characteristics of UFH and LMWH are listed for comparison (J. Hirsh and M. N. Levine, "Low molecular weight heparine", Blood 79(1): 1–17, 1992).

TABLE 1

|  | UFH | LMWH |
|---|---|---|
| Molecular weight (in Dalton) | 3000–30,000 | 2000–8000 |
| Average molecular weight (in Dalton) | 13,000 | 5000 |
| Anti-Xa/anti-IIa activity | 1:1 | 2:1–5:1 |
| Neutralization by PF 4* | strong | weak |
| Binding to proteins | high | low |
| Binding to endothelial cells | yes | weak |
| Dose-dependent clearance | yes | no |
| Bioavailability (s.c.) | 10–25% | about 90% |
| Half-lives (t½) | 1 h (i.v.) | 2 h (i.v.) |
|  | 1–2 h (s.c.) | 3–6 h (s.c.) |
| Elimination | biophasic | renal |
| Laboratory controls | required | not required |

*PF 4 = a plasma protein called platelet factor 4

In clinical applications, UFH and LMWH are essentially employed for the prophylaxis and therapy of thrombo-embolic diseases, LMWH only recently having found increased use. All in all, the peri- and post-operative thrombotic risk could be reduced by the use of these heparins from 50 to 60% to about 15 to 30% (J. Harenberg, S. Haas, and K. H. Breddin, "Prophylaxe der venösen Thrombose" in Müller-Berghaus, G. Pötsch (Ed.), "Hämostaseologie", Springer Verlag, Berlin-Heidelberg, pages 564 to 580, 1998). The achieved reduction of the peri- and post-operative thrombotic risk to 15 to 30% shows that there is a need for a further reduction of the thrombotic risk, and that is why research seeks to develop improved alternatives.

The development of hirudine, a direct thrombin inhibitor, provided some improvement because a more extensive protection became achievable. However, the use of hirudine is restricted to special problem cases, e.g., heparin intolerance, treatment of heparin-induced thrombocytopenia (HIT), because an antidote to heparin does not exist and thus there is a risk of uncontrollable bleedings.

Despite all the differences between the individual preparations, LMW heparins are rated clinically equivalent and routinely combined in meta analyses. However, they are superior to UFH in orthopedics or in surgical hip joint replacement only with respect to effectiveness, but there are no differences in tolerability. In the predominant application field of general surgery, LWMH and standard heparin prove to be constantly equivalent. This is true at least for the main criteria of antithrombotic protection and tendency to bleeding.

The equivalence of the individual LMW heparins in clinics is in contrast to the differences in average molecular weight, molecular weight spectrum, the percent anti-FXa and anti-FIIa activities and the influence on APTT, a coagulation time which indicates the inhibition of endogenous thrombin activity (by heparin). The list of differences further comprises pro-fibrinolytic activity, release of TFPI (tissue factor pathway inhibitor), influence on platelet function, etc.

To parallel the laboratory-medical variety of the individual products, there is no possibility of a superior clinical control of effectiveness which could determine the development of a new heparin.

To conclude, therefore, there are no indications of how to optimize heparins with respect to therapeutic width as a ratio of effectiveness and tolerability.

Therefore, it has been the object of the present invention to provide an active substance having anti-coagulant activity and thus to enrich the prior art by at least one further active substance, which active substance is to overcome at least part of the drawbacks known from the prior art.

Further, it has been an object of the present invention to provide a use for the active substance according to the invention.

SUMMARY OF THE INVENTION

The present object is achieved by the use of a heparin having an average molecular weight ranging from 10 to 11.5 kd for the preparation of a medicament for the prophylaxis and therapy of thrombotic processes. Preferably the heparin has an average molecular weight of 10.5 kd.

Surprisingly, it has now been found that heparin having an average molecular weight of from 10 to 11.5 kd, more preferably heparin having an average molecular weight of 10.5 kd, shows a range of activities which is clearly different from that of UFH and LMWH.

In principle, due to the suitability of LMWH and UFH, one might have expected that the heparin according to the invention, having a medium molecular weight, shows a range of activities which approximately corresponds to an average of the ranges of activities of UFH and LMWH.

Therefore, the present invention satisfies a long-standing need for improvement of the prophylaxis and therapy of thrombo-embolic processes, especially also due to the fact that, while effectiveness is increased, there is no increased tendency to bleeding as compared to the known heparins.

The evaluation of the heparin according to the invention was effected by a comparison with Enoxaparin, the internationally leading LMWH. Since LMWH are generally considered to be at least as effective and tolerable as UFH, the results obtained from a comparison between the heparin according to the invention and Enoxaparin can also be extended to UFH in some way.

For further illustration, the invention will be explained in more detail in the following in the form of examples and comparisons with the heparins known from the prior art, the following specifications being intended exclusively for further illustration of the invention and not for its limitation.

BRIEF DESCRIPTION OF THE DRAWINGS

FIG. 3b shows a representation of the anti-FXa activities of the three heparins which corresponds to that of FIG. 3a.

DESCRIPTION OF THE PREFERRED EMBODIMENTS

The heparin according to the invention was prepared by controlled depolymerization and further processed by molecular filter techniques. The thus obtained heparin had the following HPLC profile:

| | |
|---|---|
| number average molecular weight | 10,513 |
| weight average molecular weight | 10,819 |
| Z average | 11,233 |
| viscosity average | 10,819 |
| Z + 1 average | 11,815 |
| intrinsic viscosity | 0.0000 |
| peak molecular weight | 10,236 |
| dispersity | 1.029066 |
| Z average/weight average | 1.038271 |
| Z + 1 average/weight average | 1.092039 |

For further characterization and for demonstrating the superior properties of the heparin according to the invention, the heparin according to the invention was compared with an unfractionated heparin (Liquemin®) and a low molecular weight heparin (Enoxaparin).

The medium molecular weight heparin according to the invention is also referred to as "MMWH" in this description, Enoxaparin as a representative of the low molecular weight heparins is referred to as "LMWH", and Liquemin® as a representative of the unfractionated heparins is referred to as "UFH".

Figure 1:
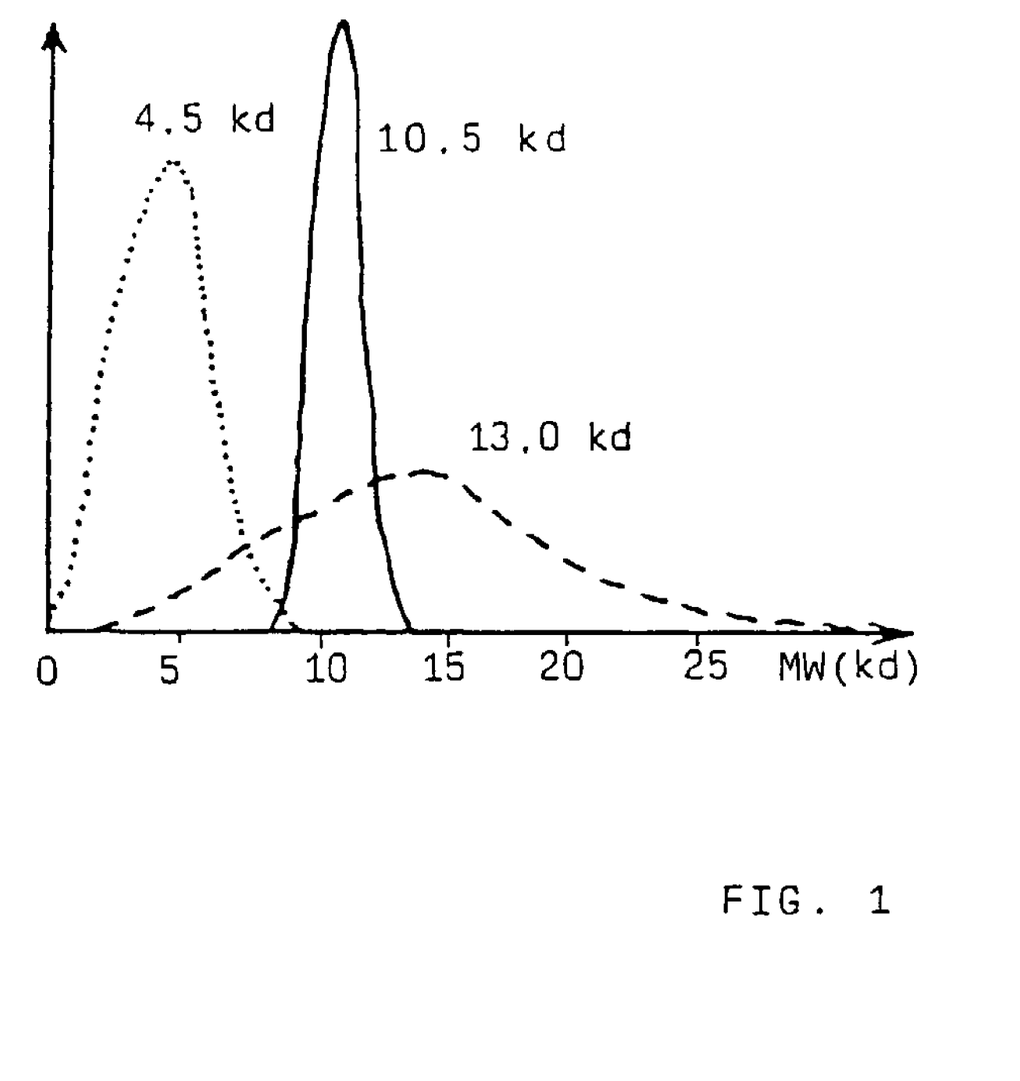
FIG. 1 shows a representation of the molecular weight distribution of the heparin according to the invention (MMWH), Enoxaparin (LMWH) and Liquemin® (UFH) in a GPC elution profile.

With respect to their molecular weights and molecular weight distributions, the heparin according to the invention, UFH and LMWH are clearly different, as can be seen from FIG. 1. From FIG. 1, which represents a GPC elution profile of the three mentioned heparins, it can be clearly seen that the UFH has an average molecular weight of 13.0 kd and at the same time a very broad molecular weight distribution. The LMWH has an average molecular weight of 4.5 kd and a clearly narrower molecular weight distribution. The heparin according to the invention, in contrast, has an average molecular weight of 10.5 kd, and it also has the narrowest molecular weight distribution of the three different heparins.

The narrow molecular weight distribution of the heparin according to the invention is of particular importance since it causes the unique and surprising range of pharmacological activities of the heparin according to the present invention.

Substantial and unexpected differences are seen from a comparison of the in-vitro activities of the three heparins. Use is made of the internationally standardized measuring system for anti-Xa activity in which the anti-Xa activity is based on 1 mg of the active substance. For comparison, measurements of anti-IIa activity were also performed. The results of this study are stated in the following Table 2.

TABLE 2

| | a-Xa IU/mg | a-IIa IU/mg | a-Xa/a-IIa ratio | a-IIa/a-Xa ratio |
|---|---|---|---|---|
| MMWH | 174.9[1] | 170.0[1] | 1.03 | 0.97 |
| Liquemin ® (UFH) | 159.0[2] | 159.0[2] | 1.00 | 1.00 |
| Enoxaparin (LMWH) | 100.0[2] | 26.3[2] | 3.80 | 0.26 |

[1]determined according to the 1st international standard for LMWH
[2]determined according to the 4th international standard for UFH It is especially surprising that the heparin according to the invention (MMWH) shows a significant increase in activity as compared to the two comparative active substances, which respectively represent a UFH and an LMWH, with respect to both anti-Xa activity and anti-IIa activity. This was by no means to be expected. At best, one could have assumed that the anti-factor-Xa and anti-thrombin activities of the heparin according to the invention would hold a position midway between those of UFH and LMWH.

A randomized multiple cross-over double-blind study was performed on 16 healthy male subjects (age: 18–32 years, weight: 64–98 kg) for the pharmacokinetic and hemostasiological characterization of the heparin according to the invention (MMWH) as compared to Liquemin® (UFH) and Enoxaparin (LMWH). Each of the subjects-received one of the three heparins as a single dose of 9000 anti-Xa IU within a one-week period. Blood was removed prior to each injection and after 0.5, 1, 2, 3, 4, 5, 8, 10 and 24 hours from each injection, and buffered with citrate. The first two milliliters of blood was discarded, and the plasma was obtained according to general directions (I. Witt, H. Beeser and G. Müller-Berghaus, "Minimalanforderungen zur Gewinnung von Citratplasma für hämostasiologische Analysen", Lab. Med., pages 143–145, 1995). The samples obtained were divided into aliquots and immediately thereafter frozen with liquid nitrogen and stored at −70° C. until the measurements were performed. The ex-vivo studies which were then performed on the blood samples were subject to the conditions described in the following.

It is to be noted that the results presented hereinafter are the results of the in-vivo effects of the heparin according to the invention (MMWH) as compared to UFH and LMWH, which were examined ex vivo.

The anticoagulant activity of the plasma samples was established by determining the coagulation time according to an APTT (activated partial thrombin time) test (APTT-Micro Kieselgur, Instrumentation Laboratory), in which the inhibition of factor Xa and of the thrombin activity was determined on an ACL 3000 model (Instrumentation Laboratory). This examination includes the determination of a coagulation parameter which is generally relied on for determining anticoagulant effects. Two values were generally determined. When the deviation was more than 3%, the measurement was repeated. The validity was determined by control experiments performed in parallel on a comparative plasma, the 4th international standard for UFH and the 1st international standard for LMWH.

For the determination of the anti-Xa and anti-IIa activities, the plasma was diluted with buffers for heparin determination (Chromogenix) and supplemented with human AT (Chromogenix). After incubation with factor Xa or thrombin (Chromogenix), the remaining activity was respectively measured using the reaction of the chromogenic substrates S2222 and S2238.

The total and free TFPI antigen concentrations in the plasma samples were measured using the specific ELISAs "Asserachrom® Free TPFI" and "Asserachrom® Total TPFI" (Diagnostica Stago). ELISA plates coated with F(ab') fragments of a TFPI-specific antibody (TT4E2) were used for the TFPI measurement. The monoclonal peroxidase-coupled detector antibodies were specific for either total TFPI (2C6) of free TFPI (H65).

The curves obtained from the studies for the prolongation of coagulation time, inhibition of factor Xa and thrombin (factor IIa), and the total and free TFPI concentrations in the individual subjects were used for determining the following pharmacokinetic parameters:

| | |
|---|---|
| $AUC_{0-24\,h}$ [s x h, % inh. x h or (ng/ml) x h] = | area under the curve |
| $c_{max}$ [s, % h inh. or ng/ml] = | activity maximum (prolongation of coagulation time, inhibition or concentration) |
| $t_{max}$ [min] = | time of activity maximum |
| $t_{½,invasion}$ [min] = | invasion half-life |
| $t_{½,elimination}$ [min] = | elimination half-life |

The values for $c_{max}$ and $t_{max}$ were directly determined from the individual curves. AUC was calculated between t=0 h and t=24 h using the trapezoidal rule.

In addition to a base value of 0, a precondition of the determination of $t_{1/2,invasion}$ and $t_{1/2,elimination}$ is that the invasion and elimination have an exponential time course. To verify these assumptions, a biexponential function was fitted to the measured data (Bateman function, extended by a log term). A comparison between the fitted and measured curves showed a very good agreement in most cases, so that the kinetics of heparin and TFPI can be described well by the Bateman function. The values of $t_{1/2,invasion}$ and $t_{1/2,elimination}$ were calculated from the constants of the Bateman functions for invasion and elimination ($k_{inv}$, $K_{el}$). All values were determined as mean values ± standard deviation. A comparison by pairs of all parameters between the three heparins was performed using a significance level (a) of 0.05. Differences were considered statistically significant if p was smaller than 0.05. The mean values of the pharmacokinetic parameters were subsequently subjected to a general linear model of variance analysis (null hypothesis: there is no difference respectively between the heparin according to the invention and Liquemin® or Enoxaparin).

Figure 2A:
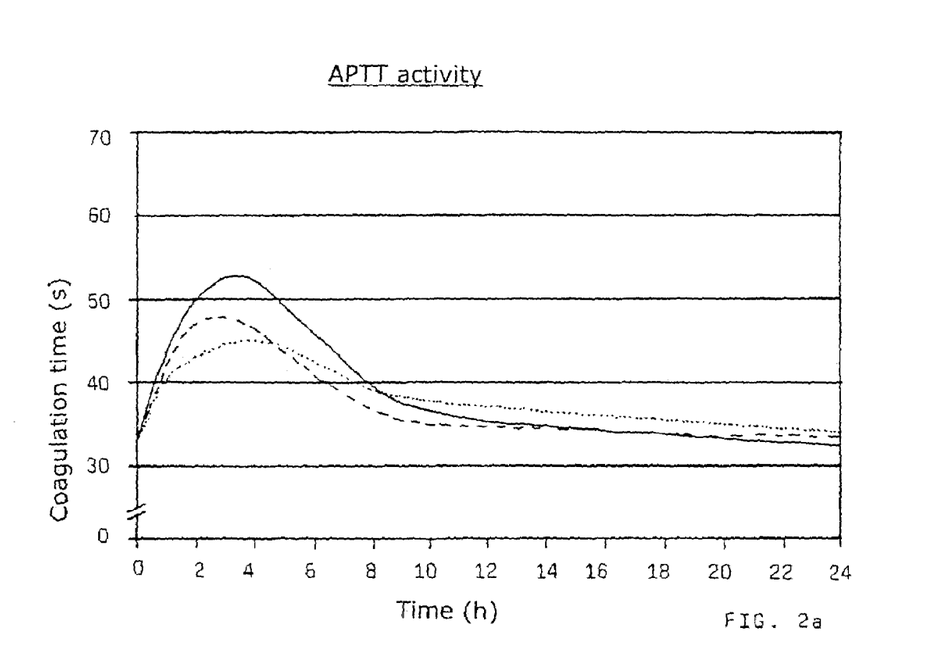
FIG. 2a shows a representation of the respective APTT activity of the heparin according to the invention (MMWH), Enoxaparin (LMWH) and Liquemin® (UFH).
Figure 2B:
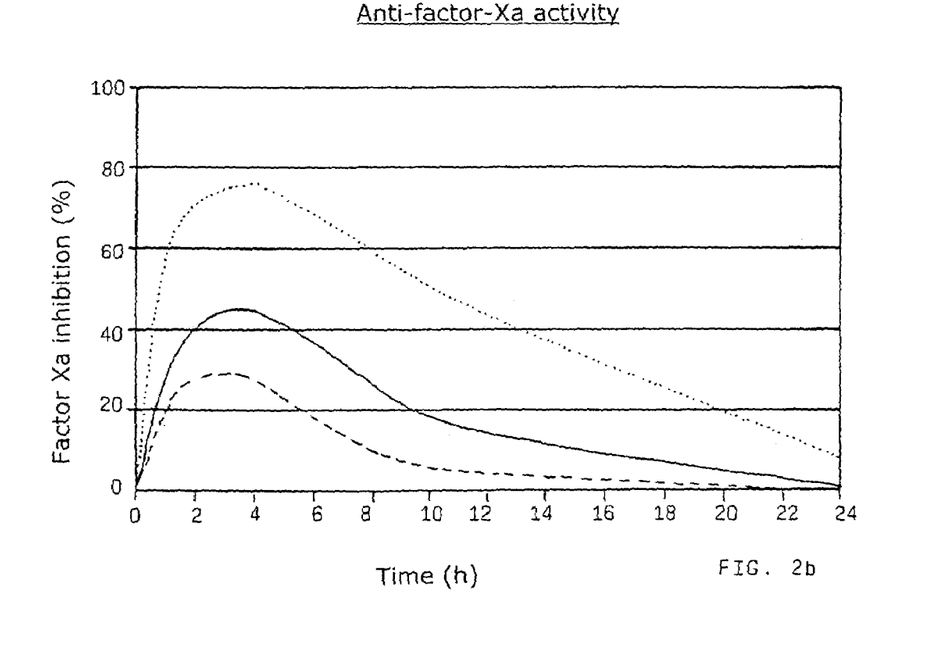
FIG. 2b shows a representation of the anti-factor-Xa activities of the three heparins.
Figure 2C:
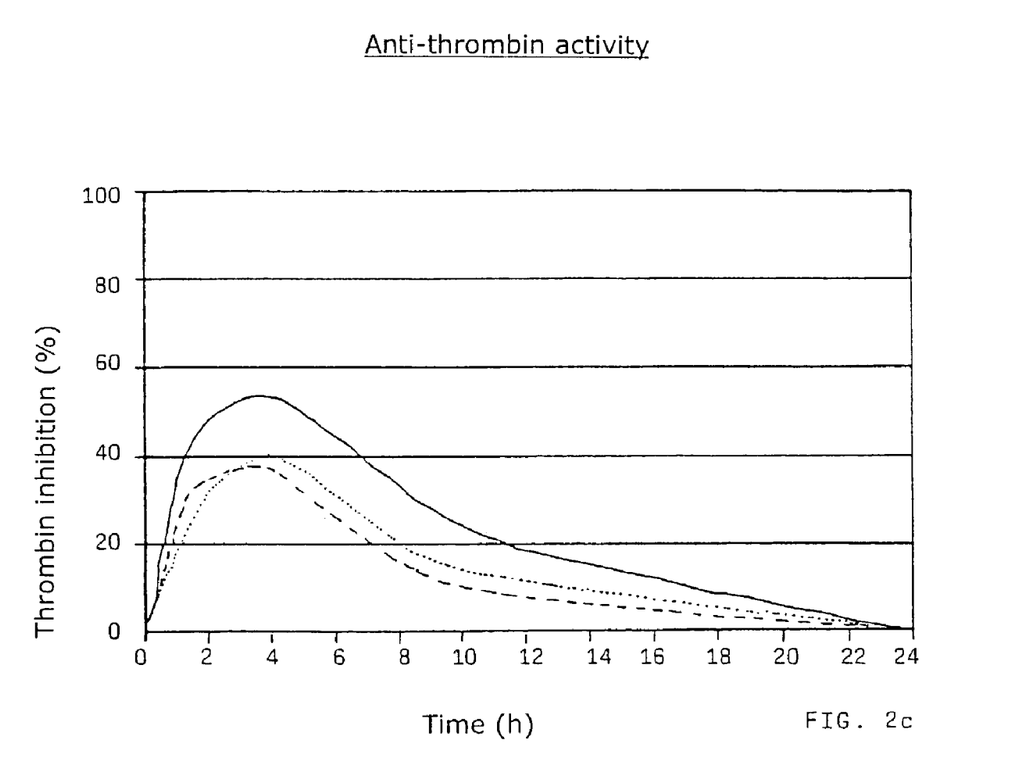
FIG. 2c shows a representation of the anti-thrombin activities of the three heparins.

As a result, it is to be noted that the curves of the effects of the three different heparins show clear and significant differences in the various studies, as can be seen from FIGS. 2a to c.

It becomes clear therefrom that the heparin according to the invention shows the highest activity in the APTT test and the anti-FIIa test and is surprisingly different from the other two heparins especially in its anti-FIIa activity. Only the anti-FXa assay shows an expected result. Here, the heparin according to the invention holds a position about midway between those of Enoxaparin and Liquemin® as examples of an LMWH and a UFH.

Figure 3A:
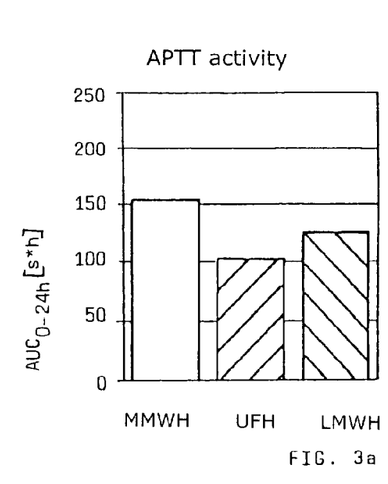
FIG. 3a shows a representation of the $AUC_{0-24h}$ values of the three heparins.
Figure 3B:
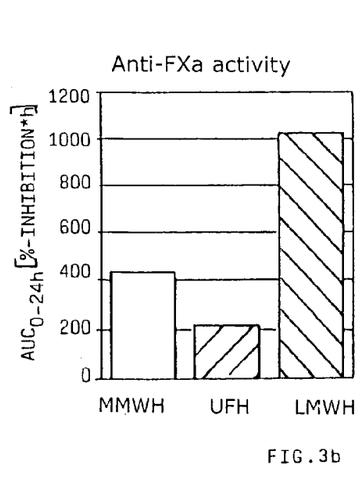
Figure 3C:
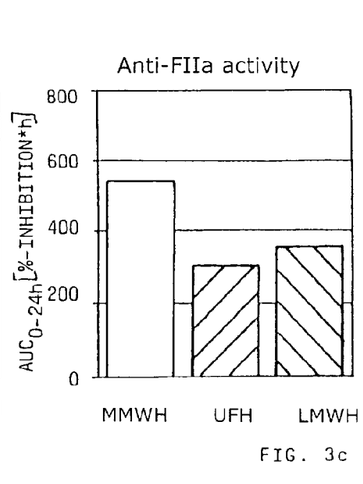
FIG. 3c shows a representation of the anti-FIIa activities of the three heparins examined which corresponds to those of FIGS. 3a and 3b.

The different anticoagulant potentials of the three heparins examined is also manifested in the $AUC_{0-24h}$ data of the APTT test and the anti-FXa and anti-FIIa assays, which are represented in FIGS. 3a to c respectively for the three heparins examined. The values result from the effect of the respective heparin in the individual tests, i.e., prolongation of coagulation time and the respective inhibition of factor Xa and thrombin. It is found that the three heparins are significantly different not only in their pharmacokinetics, but also in their pharmacodynamics (e.g., the order of magnitude of anti-FXa activity as compared to that of anti-FIIa activity).

What is striking is the fact that the activity of the heparin according to the invention as compared to Liquemin® is up to twofold respectively in all three assays. It can be concluded therefrom that the bioavailability of the heparin according to the invention, which does not contain the high molecular weight molecule typical of unfractionated heparins, is significantly higher upon subcutaneous administration. On the other hand, a comparison of the heparin according to the invention with Enoxaparin shows that the heparin according to the invention does not belong to the low molecular weight heparins. While the anti-factor-Xa activity of Enoxaparin is more than twice that of the heparin according to the invention, its anti-thrombin activity is only about 66% of that of the heparin according to the invention. It can be concluded therefrom that the bioavailability of Enoxaparin is actually higher, but that the thrombin-inhibiting activity, which is critical to anticoagulant activity, is significantly less pronounced than that of the heparin according to the invention.

The fact that the differences just described above in the in-vivo activities of Enoxaparin and the heparin according to the invention exist and are caused by the different bioavailabilities can be proven by a comparison with the already mentioned in-vitro activities of the three heparins which are stated in Table 1. Here, the situation is completely different, the heparin according to the invention showing the highest activity with respect to both anti-FXa activity and anti-thrombin activity. This difference only permits the conclusion that the influence on the result of the studies from subcutaneous administration of the three heparins to different test subjects is based on an altered availability of the active substances in the biological system, i.e., bioavailability, in contrast to the in-vitro activities.

Figure 4A:
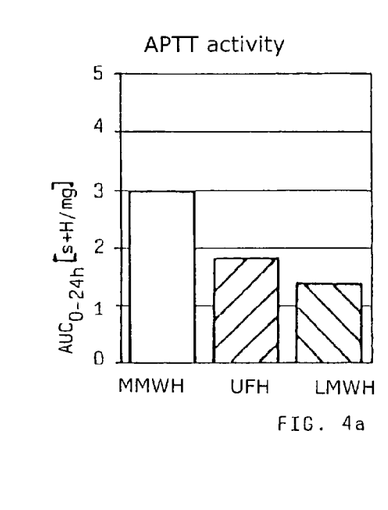
FIGS. 4a to 4c show a representation of the activities per unit dose in accordance with FIGS. 3a to c of the three heparins examined.
Figure 4B:
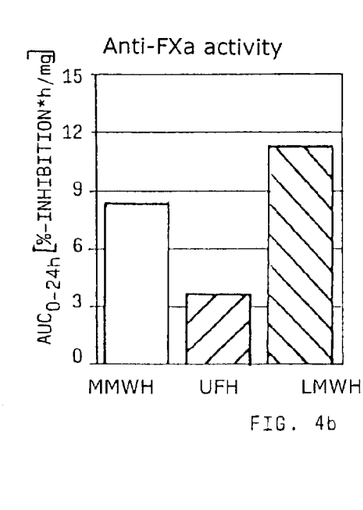
Figure 4C:
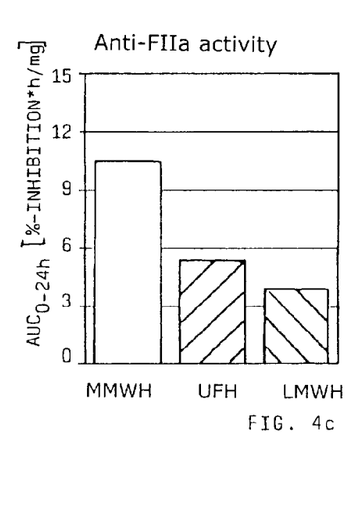

However, the values given in FIGS. 3a to 3b do not represent the mass-specific activity of every single heparin, since the specific activities of the three heparins are different, and 9000 IU of anti-FXa each of the heparin according to the invention, Liquemin® and Enoxaparin had been injected into the individual test subjects. This is also the reason why the values for $AUC_{0-24h}$ were calculated per unit dose, i.e., the value for $AUC_{0-24h}$/mg of the respectively administered heparin. The respectively administered doses were 51.5 mg of the heparin according to the invention, 56.5 mg of Liquemin® and 90 mg of Enoxaparin. A comparison of the mass-specific AUC values, represented in FIGS. 4a to 4c, clearly shows that the heparin according to the invention does not only have a higher bioavailability than that of Liquemin®, but also an essentially higher potential as compared to Enoxaparin.

When the $c_{max}$ values of the three heparins examined, which are based on a prolongation of coagulation time and inhibition, are compared, it can be seen that the values for the heparin according to the invention, such as the $AUC_{0-24h}$ values, are higher than those of Liquemin®. However, the values were higher by at most 50% (anti-FXa activity), whereas the corresponding $AUC_{0-24h}$ value was twice as high. This discrepancy is based on differences between the heparin according to the invention and Liquemin® in some pharmacokinetic parameters. In addition, the superiority of the heparin according to the invention over Liquemin®, which is more pronounced for the $AUC_{0-24h}$ value than for the $c_{max}$ value, may be of advantage because in the reverse case the risk of bleedings might be higher. By reducing the dose, $c_{max}$ can be reduced while a higher $AUC_{0-24h}$ value than that of Liquemin® is maintained.

Similarly, the discrepancy between the $c_{max}$ of Enoxaparin and Liquemin® in the anti-Xa and anti-thrombin assay is also lower than that between the $AUC_{0-24h}$ values. Despite its higher $AUC_{0-24h}$ value, the $c_{max}$ value of Enoxaparin is even 25% lower than that of Liquemin® in the APTT test. A comparison of the pharmacokinetic parameters $c_{max}$, $t_{1/2,invasion}$ [min] and $t_{1/2,elimination}$ [min] shows that the heparin according to the invention is comparable to neither UFH nor LMWH. Depending on the parameter, the heparin according to the invention is clearly distinct from either both Liquemin® and Enoxaparin (e.g., $t_{1/2,invasion}$) or only Liquemin® (e.g., $t_{max}$) or only Enoxaparin (e.g., $t_{1/2,elimination}$).

With respect to the time of the activity maximum, it may be set forth merely that the heparin according to the invention has a $t_{max}$ value which is about the same as that of Enoxaparin and is only slightly different from that of Liquemin®. In the three different assays, no significant differences could be observed for the three heparins examined.

The value for $t_{1/2,invasion}$ is significantly longer for the heparin according to the invention than that for Liquemin® in the APTT test and in the anti-FXa assay, but it is not significantly longer in the anti-FIIa assay. In addition, this time is longer than that of Enoxaparin in these two assays. However, in the anti-FIIa assay, Enoxaparin has the highest $t_{1/2,invasion}$ value, which is significant. In contrast to other time-related values, the value for $t_{1/2,elimination}$ of the heparin according to the invention is not significantly different from that of Liquemin®. The $t_{1/2,elimination}$ value of Enoxaparin is twice as high than that of the heparin according to the invention and that of Liquemin in the APTT test and in the anti-FXa assay. However, in the anti-FIIa assay, Enoxaparin has the lowest value for $t_{1/2,elimination}$. Therefore, the anti-FIIa activity of the heparin according to the invention is eliminated slowest, which is to be considered an advantage over the other two heparins due to the importance of anti-thrombin activity to the anticoagulant activity.

The above discussed values are summarized in the following in Table 3 for the three heparins examined in the three assays.

TABLE 3

| | APTT activity | | | | anti-FXa activity | | | | anti-FIIa activity | | | |
|---|---|---|---|---|---|---|---|---|---|---|---|---|
| | mean value | stand. dev. | relative | p value | mean value | stand. dev. | relative | p value | mean value | stand. dev. | relative | p value |
| | $AUC_{0-24\,h}$ [s · h]$^2$ | | | | $AUC_{0-24\,h}$ [% inhibition · h]$^3$ | | | | $AUC_{0-24\,h}$ [% inhibition · h] | | | |
| MMWH | 154 | 66 | 1.45 | | 439 | 109 | 2.00 | | 544 | 119 | 1.77 | |
| UFH | 104 | 65 | 1.00 | 0.0001 | 219 | 80 | 1.00 | 0.0001 | 308 | 115 | 1.00 | 0.0001 |
| LMWH | 126 | 55 | 1.21 | 0.0216 | 1028 | 114 | 4.69 | 0.0001 | 358 | 90 | 1.16 | 0.0001 |
| | AUC/dose [s · h/mg]$^3$ | | | | AUC/dose [% inhibition · h/mg] | | | | AUC/dose [% inhibition · h/mg]$^3$ | | | |
| MMWH | 2.99 | 1.28 | 1.63 | | 8.52 | 2.21 | 2.20 | | 10.56 | 2.31 | 1.94 | |
| UFH | 1.84 | 1.43 | 1.00 | n.d. | 3.87 | 1.42 | 1.00 | n.d. | 5.44 | 2.04 | 1.00 | n.d. |
| LMWH | 1.40 | 0.616 | 0.76 | n.d. | 11.42 | 1.27 | 2.95 | n.d. | 3.97 | 1.00 | 0.73 | n.d. |
| | $c_{max}$ [s]$^2$ | | | | $c_{max}$ [% inhibition] | | | | $c_{max}$ [% inhibition] | | | |
| MMWH | 22.7 | 10.7 | 1.30 | | 46.7 | 11.5 | 1.49 | | 55.5 | 14.3 | 1.36 | |
| UFH | 17.4 | 12.7 | 1.00 | 0.0001 | 31.4 | 12.2 | 1.00 | 0.0001 | 41.0 | 14.8 | 1.00 | 0.0001 |
| LMWH | 13.0 | 4.5 | 0.75 | 0.0216 | 77.2 | 7.9 | 2.46 | 0.0001 | 41.3 | 12.5 | 1.01 | 0.0001 |
| | $t_{max}$ [min] | | | | $t_{max}$ [min] | | | | $t_{max}$ [min] | | | |
| MMWH | 233 | 82 | 1.31 | | 218 | 43 | 1.28 | | 221 | 46 | 1.20 | |
| UFH | 178 | 73 | 1.00 | 0.0175 | 171 | 46 | 1.00 | 0.0036 | 184 | 46 | 1.00 | 0.0081 |
| LMWH | 240 | 49 | 1.35 | 0.7353 | 221 | 36 | 1.30 | 0.8070 | 248 | 37 | 1.35 | 0.0588 |
| | $t_{½,invasion}$ [min] | | | | $t_{½,invasion}$ [min] | | | | $t_{½,invasion}$ [min] | | | |
| MMWH | 105 | 17 | 1.57 | | 116 | 24 | 1.29 | | 99 | 36 | 1.18 | |
| UFH | 67 | 37 | 1.00 | 0.0003 | 91 | 26 | 1.00 | 0.0057 | 84 | 34 | 1.00 | 0.0637 |
| LMWH | 82 | 28 | 1.23 | 0.0224 | 89 | 24 | 0.98 | 0.0037 | 122 | 22 | 1.45 | 0.0082 |

TABLE 3-continued

|  | APTT activity | | | | anti-FXa activity | | | | anti-FIIa activity | | | |
|---|---|---|---|---|---|---|---|---|---|---|---|---|
|  | mean value | stand. dev. | relative | p value | mean value | stand. dev. | relative | p value | mean value | stand. dev. | relative | p value |
|  | $t_{1/2,elimination}$ [min] | | | | $t_{1/2,elimination}$ [min] | | | | $t_{1/2,elimination}$ [min] | | | |
| MMWH | 129 | 68 | 0.84 |  | 137 | 28 | 1.19 |  | 171 | 59 | 1.22 |  |
| UFH | 153 | 107 | 1.00 | 0.7753 | 115 | 40 | 1.00 | 0.2378 | 140 | 64 | 1.00 | 0.0572 |
| LMWH | 225 | 126 | 2.18 | 0.0187 | 252 | 83 | 2.19 | 0.0001 | 134 | 29 | 0.96 | 0.0239 |

[1]$p < 0.05$; significant;
[2]base of calculation: prolongation of coagulation time;
[3]administered doses: 5.5 mg of MMWH, 56.5 mg of Liquemin ® (UFH), 90.0 mg of Enoxaparin (LMWH)

Upon consideration and comparison of the total TFPI antigen concentrations and the concentrations of the free TFPI antigen after administration of the three different heparins, it is found that the concentration of the total TFPI antigen has increased to 2.0-fold to 2.5-fold of the initial value after one hour, and that the concentration of the free TFPI antigen has increased to 6.7-fold to 7.9-fold of the initial concentration. From FIGS. 5a and 5b, it can be seen that the maximum values are found after 1.5 to 2 hours, so that $t_{max}$ is significantly shorter than it was in the three assays performed previously. This shows that the heparin-induced TFPI release does not correlate with these traditional coagulation parameters.

Figure 5A:
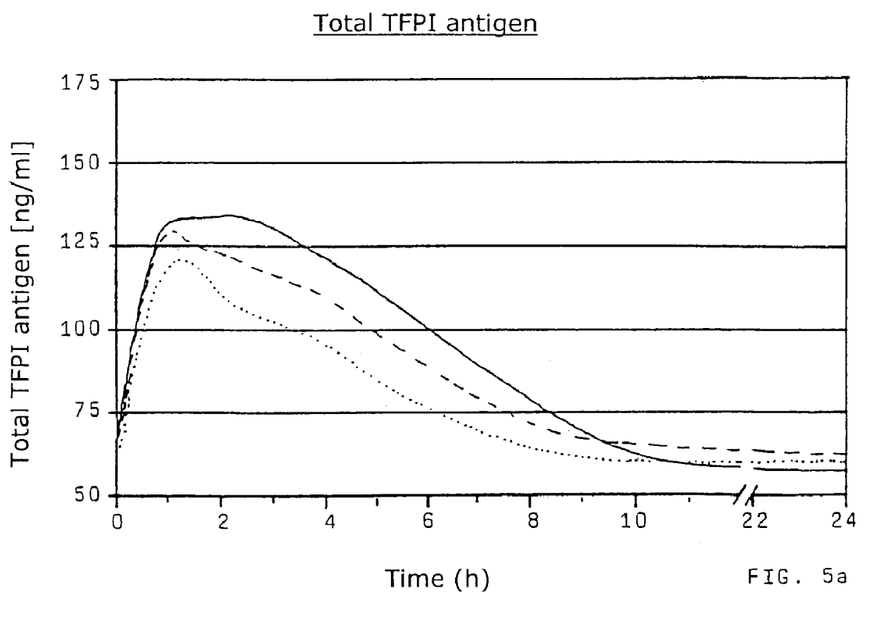
FIG. 5a shows a time-dependent representation of the concentration of total TFPI antigen respectively upon administration of a heparin (solid line: MMWH; dotted line: LMWH (Enoxaparin); dashed line: UFH (Liquemin®)).
Figure 5B:
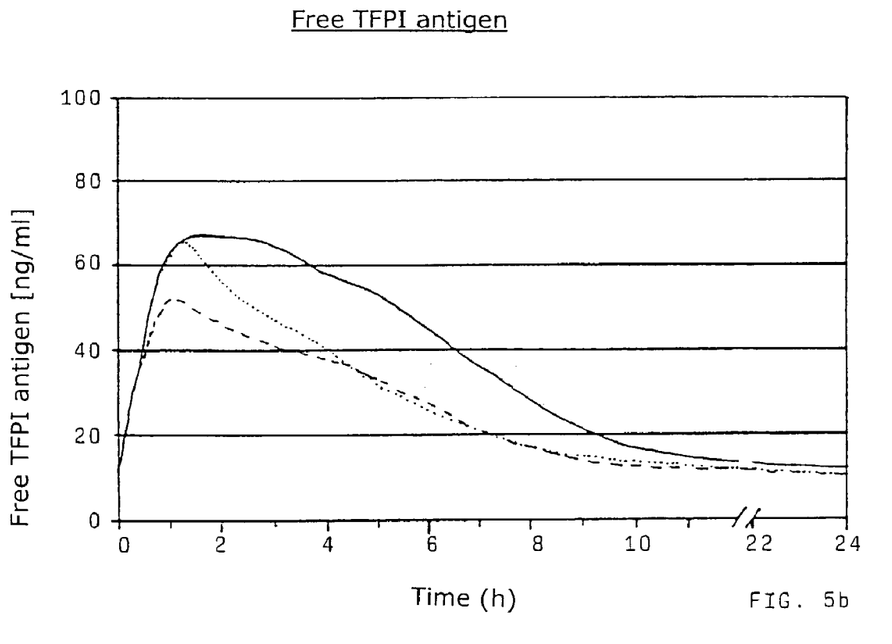
FIG. 5b shows a representation according to FIG. 5a for the free TFPI antigen.

Further, it can be seen from FIG. 5a and FIG. 5b that the activity of the heparin according to the invention is clearly different from those of Liquemin® and Enoxaparin. After administration of the heparin according to the invention, both values examined in this connection remain longer on a high level as compared with the administration of one of the comparative heparins.

This effect of the heparin according to the invention is also very surprising and of particular importance to the present invention, since especially the free TFPI antigen is considered to play an important role in coagulation.

Figure 6A:
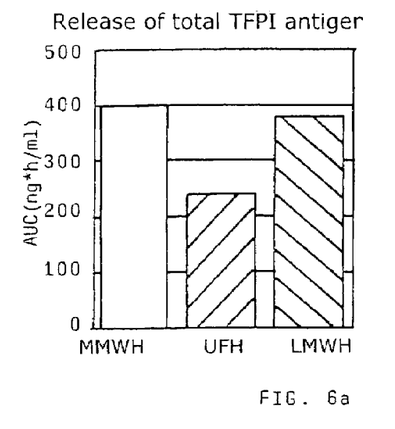
FIGS. 6a to 6d show a representation of the $AUC_{0-24}$ values for the three heparins examined, calculated from the release of total TFPI antigen and free TFPI antigen.

A comparison of the corresponding $AUC_{0-24h}$ values on the basis of the concentrations of released TFPI (for total TFPI antigen and free TFPI antigen) makes clear that the heparin according to the invention and Enoxaparin increase the plasma concentrations of the total TFPI antigen about in the same way and are clearly superior to Liquemin®, as can be seen from FIG. 6a.

Figure 6B:
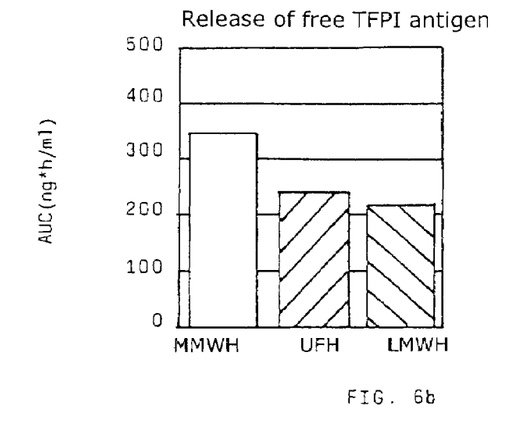

However, since the concentration of the free TFPI antigen is the parameter which is critical to coagulation where the contribution of TFPI to the activity of heparin is concerned, the $AUC_{0-24h}$ values for the concentration of the free TFPI antigen would have to be compared. From FIG. 6b, it can be seen that the heparin according to the invention is found the most effective.

Figure 6C:
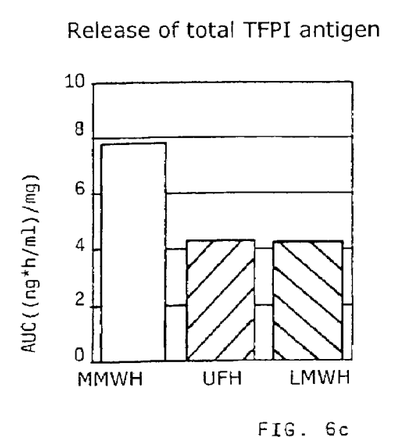
Figure 6D:
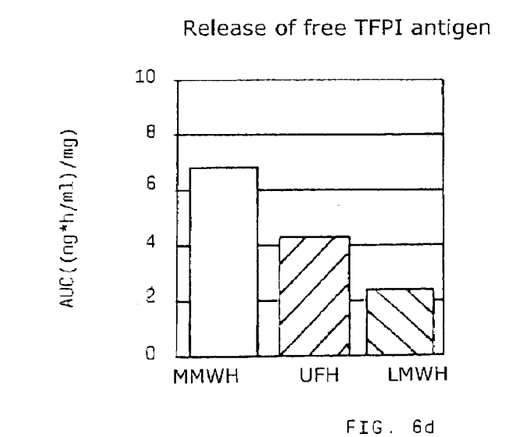

Now, when the $AUC_{0-24h}$ values per unit dose are compared on the basis of the concentrations of released TFPI, the result shown in FIGS. 6c and 6d is obtained.

Both the concentration of total TFPI antigen and the concentration of free TFPI antigen are highest for the heparin according to the invention. It is to be noted that the heparin according to the invention is clearly superior to the known heparins to an extremely and surprisingly high extent for two parameters critical to coagulation, i.e., anti-thrombin activity and release of free TFPI antigen.

Finally, it is to be mentioned that these results are confirmed by a comparison of the heparin according to the invention with Enoxaparin in an animal experiment. This animal experiment was performed on rabbits and clearly showed the better therapeutic effect of the heparin according to the invention in the prevention and treatment of thromboembolic processes as compared to low molecular weight heparins. In addition, a lower risk was found with respect to the occurrence of bleedings after the administration of the heparin according to the invention as compared to Enoxaparin.

Further, due to the examination results described above, it is preferred to employ the medium molecular weight heparin according to the invention also for the therapy of acute myocardial infarction and unstable angina, and for the inhibition of coagulation in extracorporeal circulations.

It is to be pointed out that the surprising properties of the medium molecular weight heparin according to the invention are shown, in particular, in the APTT test, which is a basic measure in heparin therapy. The coagulation time in the APTT test is significantly prolonged as compared to the examined heparins Enoxaparin and Liquemin®. The particularly high milligram activity of the heparin according to the invention, which is also completely surprising, is also of importance. Together with a significantly decreased risk of bleeding, which in an animal experiment impressively demonstrates the superiority of the medium molecular weight heparin according to the invention, completely new perspectives in heparin therapy are opened by the present invention.

With respect to activity and tolerability, the medium molecular weight heparin according to the invention was also compared to a low molecular weight heparin, i.e., Enoxaparin, in an animal experiment. This was done within the scope of a modified thrombosis model according to S. Wessler ("rabbit stasis model", "thrombosis in the presence of vascular stasis", Am. J. Med., 33: 649, 1959), wherein the experimentally induced thrombosis results from a combination of hypercoagulability and venostasis.

Two methods proven many times and well-established which served for determining the tendency to bleeding were the so-called "rabbit blood loss model" (counting of erythrocytes in the rinsing fluid after a defined injury) and the "rabbit template bleeding time" in which the bleeding time is determined (J. Fareed, J. M. Walenga et al., Studies on the antithrombotic effects and pharmacokinetics of heparin fractions and fragments, Sem. Thromb. Hemost. 11, 56–74, 1985).

Figure 7:
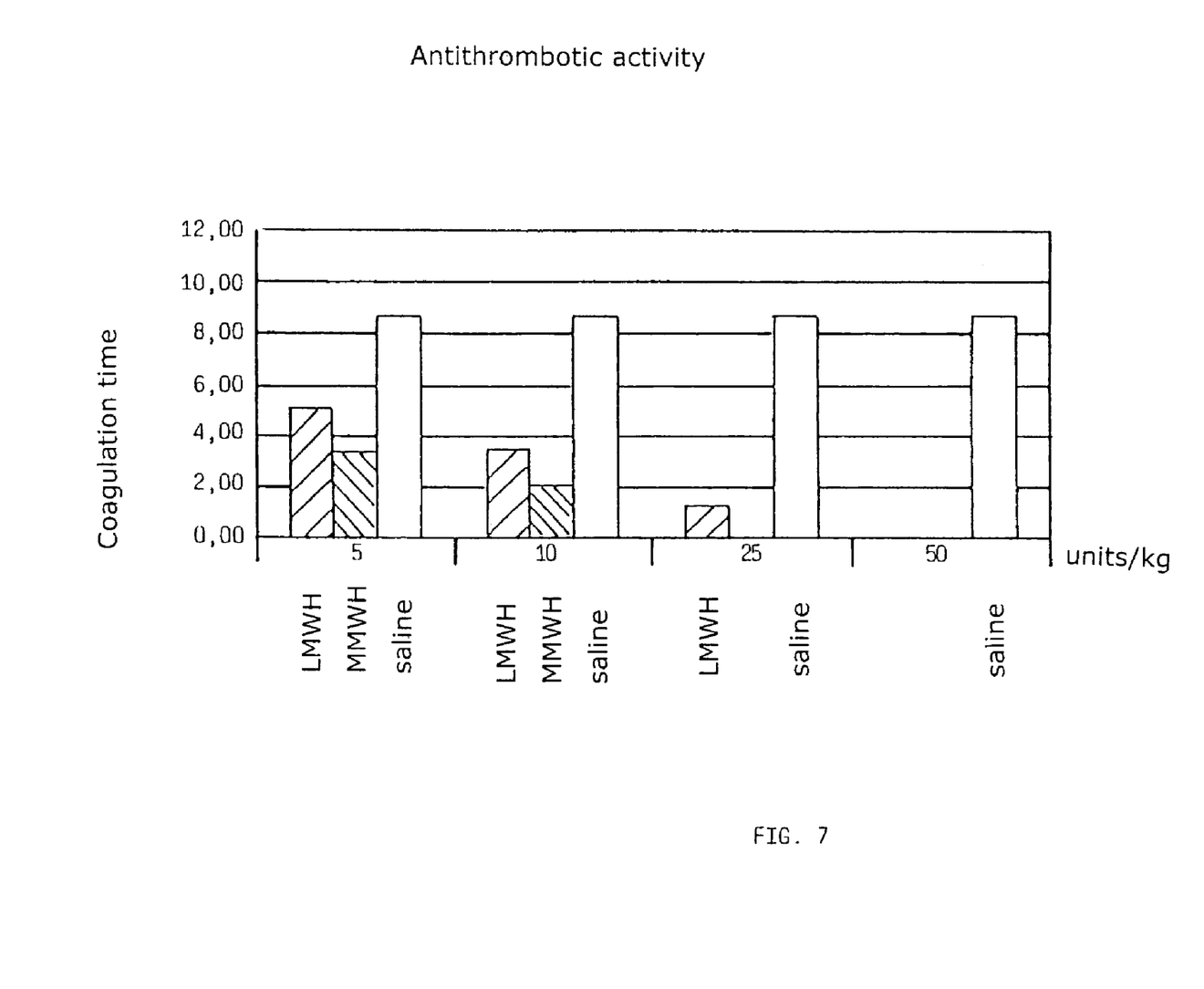
FIG. 7 shows a comparison of the antithrombotic activity of Enoxaparin and that of the medium molecular weight heparin according to the invention in an animal experiment (rabbit).
Figure 8:
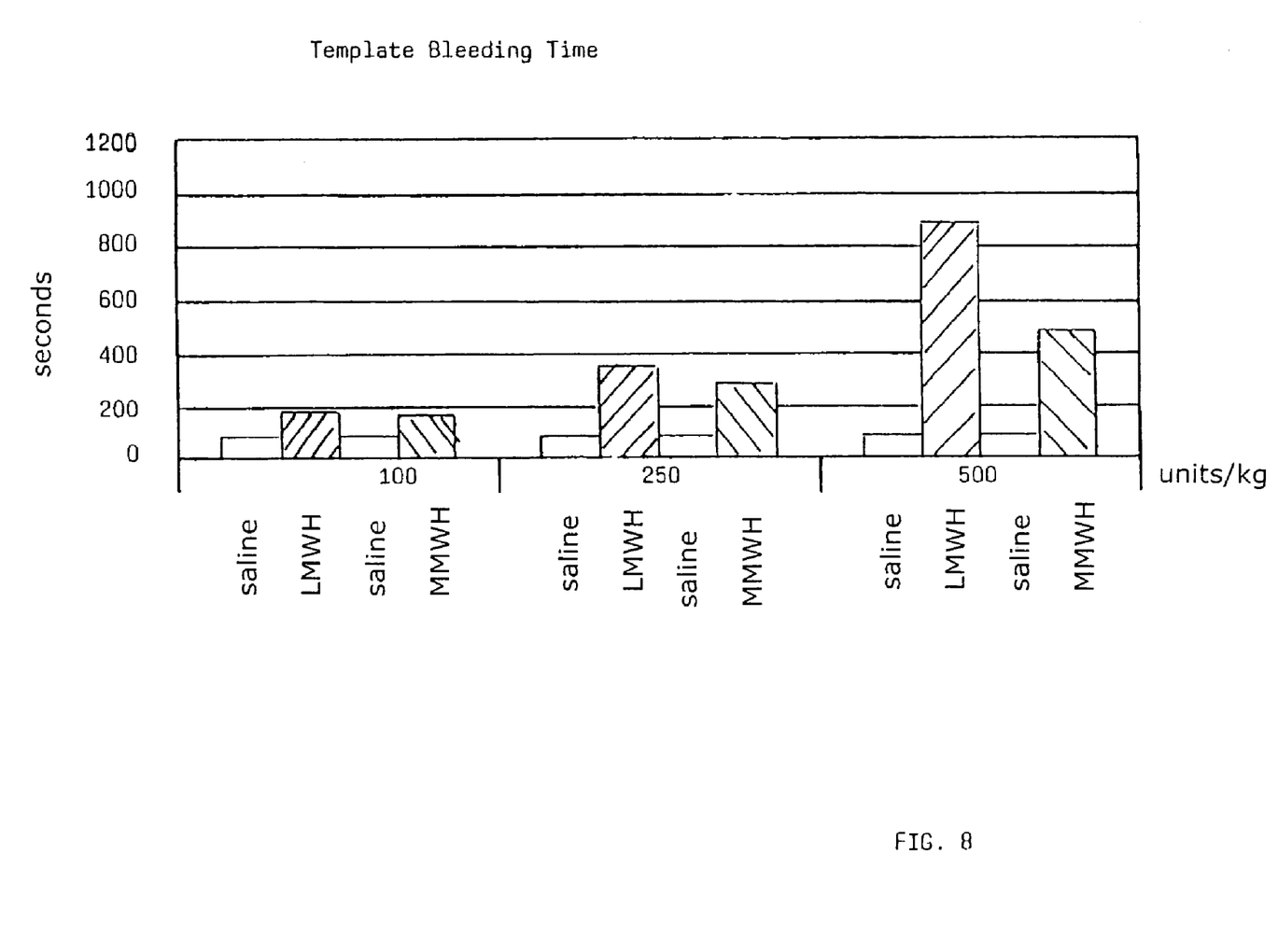
FIG. 8 shows a comparison of the duration of bleeding upon administration of Enoxaparin and the medium molecular weight heparin according to the invention in an animal model (rabbit).

FIGS. 7 and 8 prove the impressive consistent increase of the "therapeutic index" of the medium molecular weight heparin according to the invention as compared to LMWH, which is based not only on the enhanced antithrombotic activity, but also particularly on the significant reduction of the tendency to bleeding.

FIG. 7 again shows a comparison of the antithrombotic activity upon intravenous administration of Enoxaparin used as the low molecular weight heparin with that of the medium molecular weight heparin of the present invention. From the Figure, it can be seen that the coagulation value, which is a measure of the number and size of the blood clots formed, is significantly lower for the heparin according to the invention as compared to Enoxaparin. Saline was respectively used as a zero control. It was also found that clotting is completely suppressed also by Enoxaparin only at an elevated dose, which is presently at 50 units/kg of body weight.

FIG. 8 shows a comparison of the bleeding time upon intravenous administration of Enoxaparin, medium molecular weight heparin, and saline as a zero control or standard. It was found just at the higher doses that the medium molecular weight heparin according to the invention has a substantially higher potential as compared to Enoxaparin, since its absolutely lower tendency to bleeding becomes clear from the animal experiment.

Now, when these results are summarized, a so-called therapeutic index with respect to the low molecular weight heparin Enoxaparin can be established for the medium molecular weight heparin according to the invention. Thus, the data for effectiveness, i.e., antithrombotic activity, and the data for the tendency to bleeding are evaluated and correlated by means of variance analysis and linear regression. The result shows a therapeutic index of 2.24 for the medium molecular weight heparin according to the invention with respect to Enoxaparin. In other words, the medium molecular weight heparin according to the invention has an application value which is 2.24 times as high as that of Enoxaparin. These results are completely surprising to the skilled person and enable a significant improvement of heparin therapy about 60 years after the first use of unfractionated heparins and about 20 years after the first use of the low molecular weight heparins. Therefore, the present invention satisfies a long-standing need in the art.

The present invention provides a heparin which is explicitly better than those of the prior art and is characterized by a higher therapeutic index which is based on a more favorable ratio of effectiveness and tolerability. For clinical use, a greater reach in prophylaxis and therapy can be prognosticated: The medium molecular weight heparin according to the invention will be capable of being relatively higher dosed as compared to the known heparins and thus contribute to an improvement in the managing of thrombo-embolic diseases which is not yet exactly predictable.

This is unexpected for the particular reason that is cannot be derived from clinical parameters.

What is claimed is:

1. A process for treatment of thrombo-embolic processes, comprising:
    administering an effective amount of a medium molecular weight heparin (MMWH) pharmaceutical preparation to a subject in need of treatment of thrombo-embolic processes, wherein the effective amount is sufficient to treat the thrombo-embolic processes and is characterized as having the higher therapeutic index of MMWH relative to low molecular weight heparin (LMWH) and unfractionated (UFH) and the MMWH has an average molecular weight ranging from 10 to 11.5 kDa.

2. The process according to claim 1, wherein the MMWH has an average molecular weight of 10.5 kDa.

3. The process of claim 1 wherein the thrombo-embolic processes include those in acute myocardial infarction, unstable angina and coagulation in extracorporeal circulations.

4. The process of claim 1 wherein the MMWH has a a-Xa/a-IIa ratio of 1.03.

* * * * *